United States Patent [19]

Urushida

[11] Patent Number: 4,605,034

[45] Date of Patent: Aug. 12, 1986

[54] GAS FLOW CONTROL SYSTEM FOR AN ANESTHESIA APPARATUS

[75] Inventor: Yoshihisa Urushida, Tokorozawa, Japan

[73] Assignee: Citizen Watch Co., Ltd., Tokyo, Japan

[21] Appl. No.: 664,050

[22] Filed: Oct. 23, 1984

[30] Foreign Application Priority Data

Oct. 25, 1983 [JP] Japan ................................. 58-199442

[51] Int. Cl.⁴ ............................................. A61M 16/01
[52] U.S. Cl. ........................................ 137/88; 137/607
[58] Field of Search .................. 137/3, 7, 88, 607, 606

[56] References Cited

U.S. PATENT DOCUMENTS

| | | | |
|---|---|---|---|
| 3,534,753 | 10/1970 | Ollivier | 137/7 |
| 3,739,799 | 6/1973 | Bickford | 137/88 |
| 3,762,427 | 10/1973 | Mollering | 137/7 |
| 3,809,109 | 5/1974 | Breiling | 137/607 X |
| 4,015,617 | 4/1977 | Connolly | 137/88 |
| 4,237,925 | 12/1980 | Urshida | 137/607 X |
| 4,328,823 | 5/1982 | Schreiber | 137/88 |
| 4,467,834 | 8/1984 | Rochat | 137/607 |

*Primary Examiner*—Alan Cohan
*Attorney, Agent, or Firm*—Birch, Stewart, Kolasch & Birch

[57] ABSTRACT

A gas flow control system for an anesthesia apparatus, which has an oxygen gas pressure reducing valve for reducing primary pressure of oxygen gas to secondary pressure, and a anesthetic gas pressure reducing valve for reducing primary pressure of anesthetic gas to secondary pressure. A pressure control valve is connected to the secondary side of the anesthetic gas pressure reducing valve and responsive to the secondary pressure of the oxygen gas for controlling the secondary pressure of the anesthetic gas. The pressure control valve is so arranged that when the secondary pressure of the oxygen gas is zero, the pressure control valve is closed to cut off the supply of the anesthetic gas.

3 Claims, 5 Drawing Figures

GAS FLOW CONTROL SYSTEM FOR AN ANESTHESIA APPARATUS

BACKGROUND OF THE INVENTION

The present invention relates to a gas flow control system for an anesthesia apparatus of the type which operates to mix oxygen and a gaseous anesthetic such as nitrous oxide (laughing gas) and to continuously supply the gaseous mixture.

In the anesthesia apparatus of the continuous flow type, flow regulating valves are provided in an oxygen line and gaseous anesthetic line, respectively, so as to regulate the flow rate of each gaseous component. However, it is difficult to regulate the total flow rate and the proportions of the gaseous components to desired values by operating the two flow regulating valves. In recent years, a gas flow control system for an anesthesia apparatus in which the total flow rate and the mixing ratio of the gaseous components can be separately regulated has been used. However, the system has a disadvantage in that the safety during anesthetization is not ensured with failure of elements in the system.

SUMMARY OF THE INVENTION

An object of the present invention is to provide a gas flow control system provided with means for preventing the leakage of a gaseous anesthetic from the system when an element of the system fails to operate properly.

Another object of the present invention is to provide a gas flow control system for an anesthesia apparatus which may be easily operated to regulate the total flow rate of gaseous components and proportions thereof.

According to the present invention, there is provided a gas flow control system for an anesthesia apparatus, comprising an oxygen circuit between an oxygen gas inlet and a manifold, a gaseous anesthetic circuit between an anesthetic gas inlet and the manifold, an oxygen gas pressure reducing valve provided in the oxygen circuit for reducing primary pressure of the oxygen gas supplied from the inlet to secondary pressure, an oxygen gas flow regulating valve connected between a secondary side of the oxygen gas pressure reducing valve and the manifold for regulating the flow rate of the oxygen gas, and an anesthetic gas pressure reducing valve provided in the gaseous anesthetic circuit for reducing primary pressure of the anesthetic gas to secondary pressure. The system has a pressure control valve connected to the secondary side of the anesthetic gas pressure reducing valve and responsive to the secondary pressure of the oxygen gas for controlling the secondary pressure of the anesthetic gas, an anesthetic gas flow regulating valve connected between a secondary side of the pressure control valve and the manifold for regulating the flow rate of the anesthetic gas and means for operating the oxygen gas flow regulating valve and the anesthetic gas flow regulating valve and for controlling flow rates of both gases. The pressure control valve is so arranged that when the secondary pressure of the oxygen gas is zero, the pressure control valve is closed to cut off the supply of the anesthetic gas.

These and other objects and features of the present invention will become more apparent from the following description with reference to the accompanying drawings.

DESCRIPTION OF THE PREFERRED EMBODIMENTS

Figure 1:
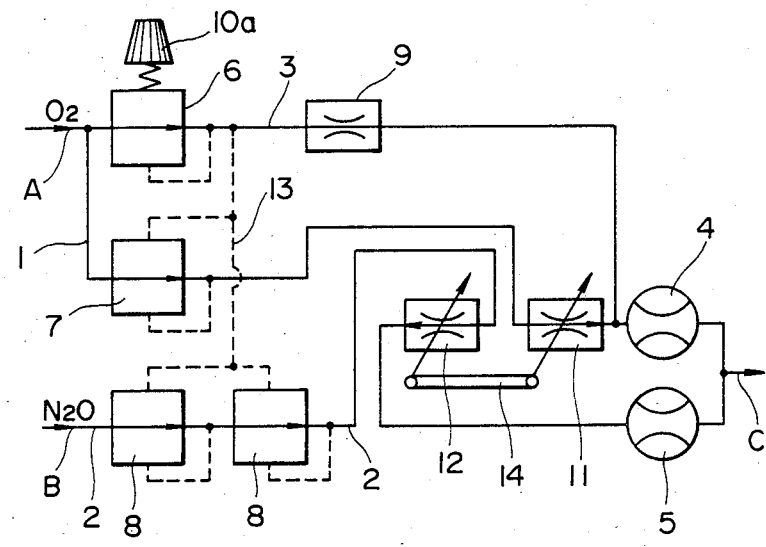
FIG. 1 is a schematic diagram showing a conventional gas flow control system for an anesthesia apparatus.

FIG. 1 shows a gas flow control system for an anesthesia apparatus disclosed in U.S. Pat. No. 3,739,799. The system comprises an oxygen circuit 1, nitrous oxide circuit 2, and bleed circuit 3. The oxygen circuit 1 comprises an oxygen inlet A, oxygen gas pressure reducing valve 7, oxygen gas flow regulating valve 11, and oxygen gas flowmeter 4, in series, and is connected to a manifold C. The nitrous oxide circuit 2 includes a nitrous oxide gas inlet B, nitrous oxide gas pressure reducing valves 8 which are connected in series, nitrous oxide gas flow regulating valve 12, and flowmeter 5 connected to the manifold C. The bleed circuit 3 comprises a flow regulating device 6 with a pressure reducing valve regulated by a knob 10a, and an orifice 9 which is connected to the inlet of the flowmeter 4. A pilot pressure line 13 is provided to apply the output pressure of the flow regulating device 6 to pressure reducing valves 7 and 8. Regulating elements of both flow regulating valves 11 and 12 are connected by a mixing ratio regulating member 14 and arranged such that when one of valves opens, the other closes without affecting the total flow rate.

In operation, oxygen gas and nitrous oxide gas are supplied to inlets A and B at predetermined pressures, respectively. The pilot pressure of oxygen gas in the pilot pressure line 13 is varied by the flow regulating device 6, so that pressure reducing valves 7 and 8 operate to vary the flow rates of oxygen gas and nitrous oxide sent to the flow regulating valves 11 and 12 while keeping pressures of both gases at a constant value. In order to vary the proportions of oxygen gas and nitrous oxide gas, the proportions of flow rates of both gases passing through the flow regulating valves 11 and 12 are varied by operating the regulating member 14.

In the system, if the oxygen gas pressure reducing valve 7 breaks down to fail to supply the oxygen gas to the flow regulating valve 11, only nitrous oxide gas flows from the system. This is very dangerous. On the other hand, if the flow regulating valve 11 or 12 is not properly adjusted or not perfectly closed because of the wear of a part of the valve, the leakage of nitrous oxide gas may result, even if the nitrous oxide gas flow regulating valve 12 is set to zero percent.

The present invention provides a control system which prevents the occurence of the above described dangerous situations.

Figure 2:
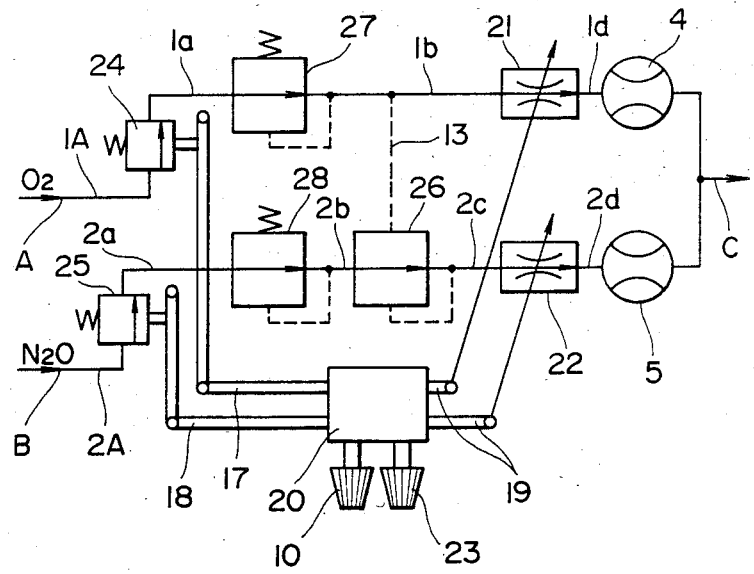
FIG. 2 is a schematic diagram showing a gas flow control system according to the present invention.

Referring to FIG. 2, the system of the present invention comprises an oxygen circuit and a nitrous oxide circuit. The oxygen circuit includes an oxygen inlet A communicated with an oxygen source, line 1A, oxygen valve 24, line 1a, oxygen gas pressure reducing valve 27, line 1b, oxygen gas flow regulating valve 21, line 1d, and flowmeter 4, which are connected in series to a manifold C. The nitrous oxide circuit comprises a nitrous oxide gas inlet B communicated with a nitrous oxide source, line 2, nitrous oxide valve 25, line 2a, nitrous oxide gas pressure reducing valve 28, line 2b, nitrous oxide gas pressure control valve 26, line 2c, nitrous oxide gas flow regulating valve 22, line 2b, flowmeter 5, which are connected in series to the manifold C. A flow-rate-mixing-ratio-control device 20 is provided to operate oxygen valve 24, nitrous oxide valve 25, and flow regulating valves 21 and 22. The control device 20 has a flow regulating knob 10 operatively connected to flow regulating valves 21 and 22 through control actuating members 19, respectively, so as to regulate the flow rate of each gaseous component. Further, the control device 20 has a mixing ratio adjusting knob 23 operatively connected with valves 24 and 25 and flow regulating valves 21 and 22 through actuating members 17 and 18, respectively. The control device 20 is so arranged to vary the total flow rate, keeping the proportions of oxygen gas and nitrous oxide gas to constant values, and to vary the proportions without affecting the total flow rate. Such a mechanism is disclosed in U.S. Pat. No. 4,237,925 (FIGS. 6 and 7).

Figure 4:
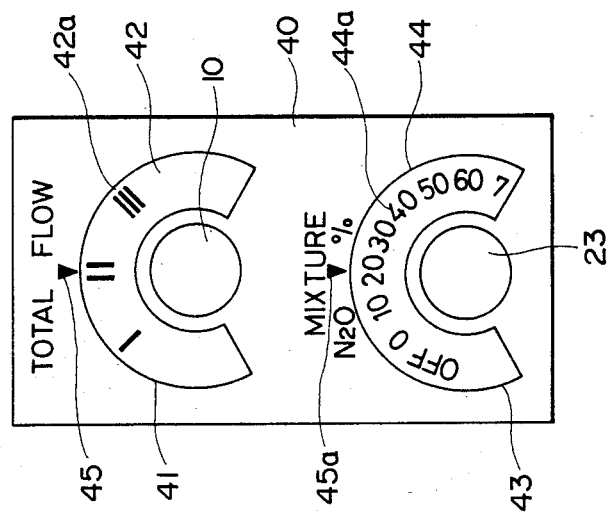
FIG. 4 is a front view of a flow control device in the system of the present invention.

As shown in FIG. 4, the control device 20 has an indication panel 40 which has a transparent window 41 for a total flow rate dial 42 bearing flow rate indications 42a and a transparent window 43 for mixing ratio dial 44 bearing mixing ratio indications 44a and "OFF" mark. Further, the indication panel 40 has point marks 45 and 45a. The mixing ratio indications 44a designate nitrousoxide-gas to oxygen-gas ratio, that is nitrous oxide concentrations (%).

Figure 5:
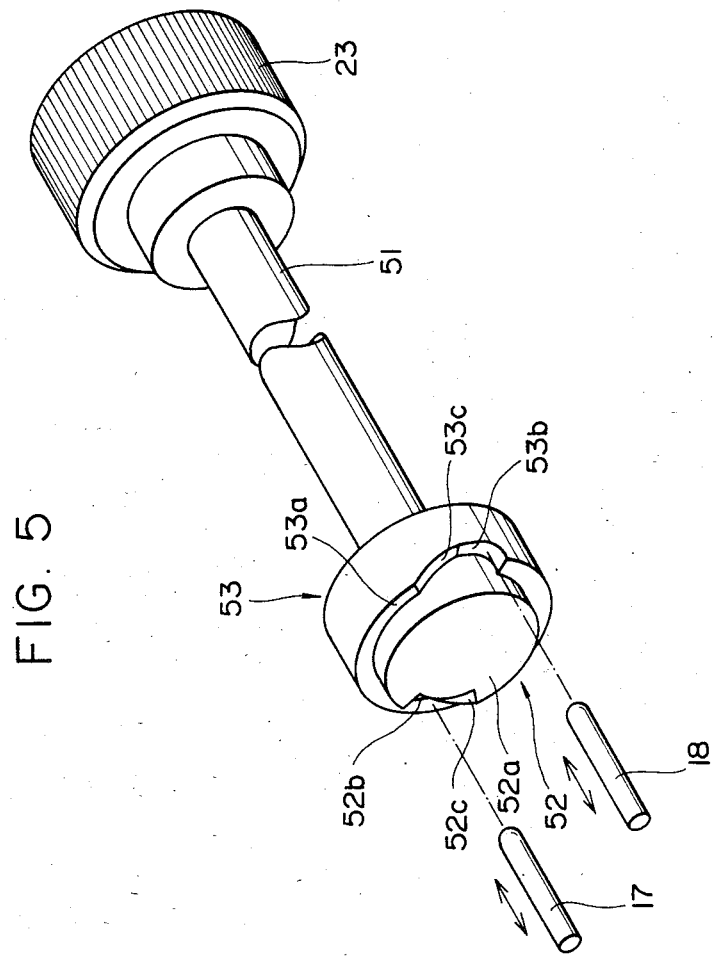
FIG. 5 is a perspective view showing a cam mechanism for an oxygen valve and nitrous oxide valve.

FIG. 5 shows a cam mechanism for operating oxygen valve 24 and nitrous oxide valve 25. A shaft 51 of the mixing ratio adjusting knob 23 is provided with an oxygen valve cam 52 and a nitrous oxide cam 53. Between the knob 23 and the cams 52, 53, a link mechanism for operating flow regulating valves 21 and 22 is provided. The mechanism may be the device of FIGS. 6 and 7 in U.S. Pat. No. 4,237,925 as described above. On the cam 52, the actuating member 17 engages, and actuating member 18 is engaged with the cam 53. Each cam has a lobe portion (52a, 53a) having a constant life, indentation (52b, 53b) and slant (52c, 53c).

When the knob 23 is at the "OFF" position, the actuating members 17 and 18 are respectively in indentations 52b and 53b as shown in FIG. 5. In that position, the oxygen valve 24 and nitrous oxide valve 25 are closed. When the knob 23 is rotated to the "0"% position, the actuating member 17 is elevated by the lobe portion 52a, so that only oxygen valve 24 is opened to supply oxygen gas. When the knob 23 is further rotated to a low concentration position, for example 3 to 5% position, the actuating member 18 is elevated by the lobe portion 53a, which causes nitrous oxide valve 25 to open to supply the nitrous oxide gas. The concentration at which the nitrous oxide valve 25 is opened can be changed by adjusting the actuating member 18.

Another mechanism for operating the valves 24, 25 can be employed. In another device, the knob 23 can be pulled to open the oxygen valve 24 at the 0% position and pushed to close the valve. In such a device, the "OFF" indication is removed. The concentration of nitrous oxide gas can be varied up to 70%. This is to prevent the danger that the oxygen supply might become extremely insufficient, if the concentration is increased more than the value.

The pressure reducing valve 27 is adapted to reduce oxygen gas pressure of about 4 $Kg/cm^2$ at the primary side to secondary pressure of about 0.6 $Kg/cm^2$. The oxygen gas having the secondary pressure is supplied to the flow regulating valve 21 and also to the pressure control valve 26 passing through the line 13, as pilot pressure. Similarly, the pressure reducing valve 28 acts to reduce nitrous oxide gas pressure of about 4 $Kg/cm^2$ at the primary side to secondary pressure of about 0.85 $Kg/cm^2$ and supply the gas to the pressure control valve 26. The pressure reducing valves 27 and 28 are the same in construction and each valve has a conventional structure in which the secondary pressure can be varied by adjusting spring force. The ratio between the rated secondary pressures is decided by the ratio between specific gravities of both gases.

The pressure control valve 26 is a safety device for controlling the pressure of nitrous oxide gas in accordance with the pressure of oxygen gas applied through the line 13. When secondary pressure of oxygen gas from the pressure reducing valve 27 is at the rated pressure of about 0.6 $kg/cm^2$, the pressure control valve 26 is fully opened, so that nitrous oxide gas having secondary pressure of about 0.85 $kg/cm^2$ is supplied to the flow regulating valve 22. If the secondary pressure of oxygen gas reduces for some failure, the pressure control valve 26 reduces the secondary pressure of nitrous oxide gas at the same reduction rate as the oxygen gas. When the secondary pressure of oxygen gas is at zero, nitrous oxide gas supply is cut off.

Figure 3:
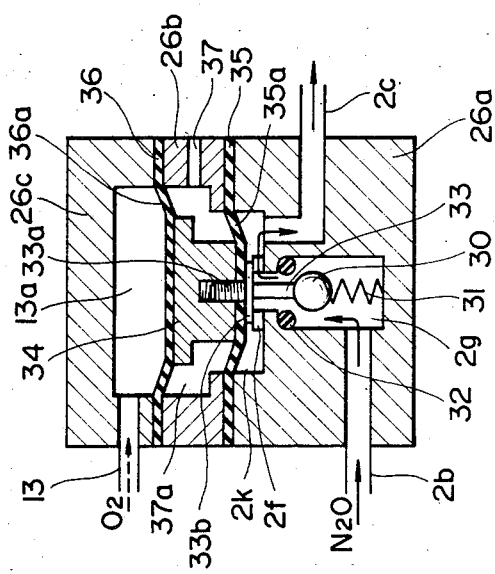
FIG. 3 is a sectional view showing a nitrous oxide gas pressure control valve in the system of the present invention.

FIG. 3 shows the construction of the pressure control valve 26. The valve has a valve body comprising a base body 26a, intermediate frame 26b, and cover 26c. A diaphragm 35 is provided between the base body 26a and intermediate frame 26b, and a diaphragm 36 is provided between the intermediate frame 26b and cover 26c. Diaphragms 35 and 36 serve as packings and define an oxygen gas chamber 13a communicated with the line 13, a nitrous oxide gas chamber 2k communicated with the line 2b, and an air chamber 37a communicated with the atmosphere through a hole 37 formed in the intermediate frame. Since the air chamber 37a is disposed between chambers 13a and 2k, even if diaphragm 35 or both diaphragms 35, 36 break, nitrous oxide gas is discharged to the atmosphere without mixing with oxygen gas. The base body 26a has a gas chamber 2g to the upper wall of which a valve seat 32 is secured. The gas chamber 2g is communicated with the gas chamber 2k. Provided in the gas chamber 2g is a valve ball 30 urged to the valve seat 32 by a spring 31. A valve shaft 33 of the valve ball 30 is secured to a spacer 34 between diaphragms 35 and 36 by a screw portion 33a. In the gas chamber 2K, a plurality of projections are annularly disposed on the base body 26a to form a plurality of gas passages 2f there-between.

In the system of the present invention, the pressure of nitrous oxide gas (0.85 $Kg/cm^2$) in the gas chamber 2k is higher than the oxygen gas pressure (0.6 $kg/cm^2$) in the gas chamber 13a. Accordingly, the pressure receiving area of the diaphragm 36 is increased compared with that of the diaphragm 35 so that the ratio between the areas becomes approximately equal to the reciprocal of the ratio between the gas pressures (the raio between the area is about 1.43). The area of the spacer 34 at the portion engaged with the disphragm 35 is reduced to aid the area effect of the diaphragm. On the other hand, each of flexible portions 35a and 36a of diaphragms 35 and 36 is provided to have the necessary size.

When the oxygen gas pressure in the gas chamber 13a is at zero, the valve ball 30 is pressed against the valve seat 32 by the spring 31 to close the valve port to cut off the nitrous oxide gas supply. Thus, the danger of supplying nitrous oxide gas only can be prevented. When the oxygen gas has a pressure in the gas chamber 13a, the valve ball 30 is removed from the valve seat 32, so that the nitrous oxide gas flows into the gas chamber 2k and into the line 2c as shown by arrows. Thus, the pressure in the gas chamber 2g decreases and the pressure in the gas chamber 2k is kept at a value slightly higher than the oxygen gas pressure to balance with the oxygen gas pressure. Accordingly, the pressure of the nitrous oxide gas is kept at a predetermined value. When the oxygen gas pressure is at a rated value, a disc 33b of the valve shaft 33 is abutted on projections 2f to widely open the valve port. Thus, the nitrous oxide gas flows passing through the valve port without variation of the pressure.

Flow regulating valves 21 and 22 are the same in shape and size and so arranged that when the oxygen gas and the nitrous oxide gas are supplied at the rated pressures (0.6 kg/cm$^2$ and 0.85 kg/cm$^2$), opening degrees of both valves are equal, thereby supplying both gases at equal flow rates. Further, each of the flow regulating valves 21 and 22 is so arranged that the flow rate is proportional to the opening degree of the valve. Such a valve is disclosed in FIGS. 2 to 5 of U.S. Pat. No. 4,237,925. Accordingly, if the indications 42a of the dial 42 are made to indicate actual flow rate, the flowmeters 4 and 5 can be omitted.

The control device 20 is provided with a link mechanism responsive to indications on total flow rate dial 42 and mixing ratio dial 44 dependent on operations of knobs 10 and 23 for controlling opening degrees of flow regulating valves 21 and 22 through actuating member 19, respectively, thereby deciding total flow rate and mixing ratio.

In the conventional system of FIG. 1, the flow rate by the flow regulating valve 11 (12) is not proportional to the opening degree of the valve. Accordingly, in the conventional system, the total flow rate can not be decided by operating the flow regulating valve. Therefore, the total flow rate is decided by manually adjusting the flow regulating valve according to indication of the flowmeter.

In the system of the present invention, since flow rates of the flow regulating valves are proportional to opening degrees of the valves, total flow rate can be controlled by oeerating the knob 10. Accordingly, manipulation of the system is very simplified.

Total flow rates for the infant, adult female and adult male can be set to 5 l/min, 7.5 l/min and 10 l/min, respectively, without considering individualities. Accordingly, in the system of the present invention, if the total flow rate indication 42a is so designed as to indicate total flow rate corresponding to the total opening degree of flow regulating valves 21 and 22, the total flow rate can be set before the operation of the system and it is not necessary to set the total flow rate at every operation. Thus, manipulation of the system is simplified. Although the total flow rate indication may be numeral indicating the value, marks of I, II and III for the above described three levels as shown in FIG. 4 can be used.

From the foregoing, it will be understood that the present invention provides a gas flow control system provided with a nitrous oxide gas pressure control valve which is controlled by the secondary pressure of oxygen gas and closed when the secondary pressure is zero. Accordingly, the leakage of nitrous oxide can be prevented.

While the invention has been described in conjunction with preferred specific embodiments thereof, it will be understood that this description is intended to illustrate and not limit the scope of the invention, which is defined by the following claims.

What is claimed is:

1. A gas flow control system for an anesthesia apparatus, comprising:

an oxygen circuit between an oxygen gas inlet and a manifold;

a gaseous anesthetic circuit between an anesthetic gas inlet and said manifold;

an oxygen valve connected to said oxygen gas inlet for controlling the supply of oxygen gas;

an anesthetic valve connected to said anesthetic gas inlet for controlling the supply of anesthetic gas;

an oxygen gas pressure reducing valve provided in said oxygen circuit for reducing primary pressure of said oxygen gas supplied from said oxygen valve to secondary pressure;

an oxygen gas flow regulating valve connected between a secondary side of said oxygen gas pressure reducing valve and said manifold for regulating the flow rate of said oxygen gas;

an anesthetic gas pressure reducing valve provided in said gaseous anesthetic circuit for reducing primary pressure of the anesthetic gas to secondary pressure;

a pressure control valve connected to the secondary side of said anesthetic gas pressure reducing valve and responsive to said secondary pressure of the oxygen gas for controlling said secondary pressure of said anesthetic gas;

an anesthetic flow regulating valve connected between a secondary side of said pressure control valve and said manifold for regulating the flow rate of said anesthetic gas; and means for operating said oxygen gas flow regulating valve and said anesthetic gas flow regulating valve and for controlling flow rates of both gases;

said means having a knob for operating said oxygen valve, said knob having a cut off position, and said means being so arranged that when said knob is at the cut off position, both the oxygen valve and anesthetic valve are closed, when said knob is operated a predetermined small degree, said oxygen valve is opened, and when said knob is operated more than said predetermined degree, said anesthetic valve is also opened.

2. The gas flow control system according to claim 1, wherein said pressure control valve is so arranged that when the secondary pressure of the oxygen gas is zero, the pressure control valve is closed to cut off the supply of said anesthetic gas.

3. The gas flow control system according to claim 1, wherein said pressure control valve comprises a valve body, a diaphragm provided in said valve body so as to be deflected by said secondary pressure of said oxygen gas, a passage for said anesthetic gas formed in said valve body, a valve provided in said passage and operatively connected to said diaphragm, and a spring biasing said valve to close said passage when said secondary pressure is zero.

* * * * *